United States Patent
Beatson et al.

(10) Patent No.: US 6,870,684 B2
(45) Date of Patent: Mar. 22, 2005

(54) MULTI-WAVELENGTH APERTURE AND VISION SYSTEM AND METHOD USING SAME

(75) Inventors: David T. Beatson, Kennett Square, PA (US); Christian Hoffman, Willow Grove, PA (US)

(73) Assignee: Kulicke & Soffa Investments, Inc., Wilmington, DE (US)

(*) Notice: Subject to any disclaimer, the term of this patent is extended or adjusted under 35 U.S.C. 154(b) by 5 days.

(21) Appl. No.: 10/418,803

(22) Filed: Apr. 18, 2003

(65) Prior Publication Data

US 2003/0202252 A1 Oct. 30, 2003

Related U.S. Application Data

(63) Continuation-in-part of application No. 10/336,458, filed on Jan. 3, 2003, now Pat. No. 6,760,161, which is a continuation of application No. 09/961,742, filed on Sep. 24, 2001, now Pat. No. 6,529,333.

(51) Int. Cl.[7] .......................... G02B 27/14; G02B 3/00; G02B 13/00
(52) U.S. Cl. ....................................... 359/634; 359/722
(58) Field of Search ................................ 359/618, 629, 359/634–636, 722, 723, 738, 802; 356/414, 418, 419; 353/31–34, 37, 38; 250/208.1, 223 R, 216, 221

(56) References Cited

U.S. PATENT DOCUMENTS

| | | |
|---|---|---|
| 3,895,854 A | 7/1975 | Ziffer |
| 5,048,926 A | 9/1991 | Tanimoto |
| 5,515,169 A | 5/1996 | Cargill et al. |
| 5,751,473 A | 5/1998 | Runciman |
| 5,982,493 A | 11/1999 | Lehnen et al. |
| 6,008,943 A | 12/1999 | Metelitsa |
| 6,407,867 B1 | 6/2002 | Hildebrandt |

Primary Examiner—Georgia Epps
Assistant Examiner—Alicia M. Harrington
(74) Attorney, Agent, or Firm—RatnerPrestia

(57) ABSTRACT

A method and system for providing different images representing plural depths of field of an electronic device. The vision system has a beamsplitter for receiving an image of the device illuminated by the at least one light source, the beamsplitter providing one of the plurality of images of the device based in a wavelength of the light source; an aperture having a plurality of effective diameters based on the wavelength of light from the at least one light source, the aperture determining a depth of field of the image of the device; and an optical element for receiving the image of the device, the optical element magnifying the image by a predetermined magnification factor to produce a magnified image having the determined depth of field.

23 Claims, 12 Drawing Sheets

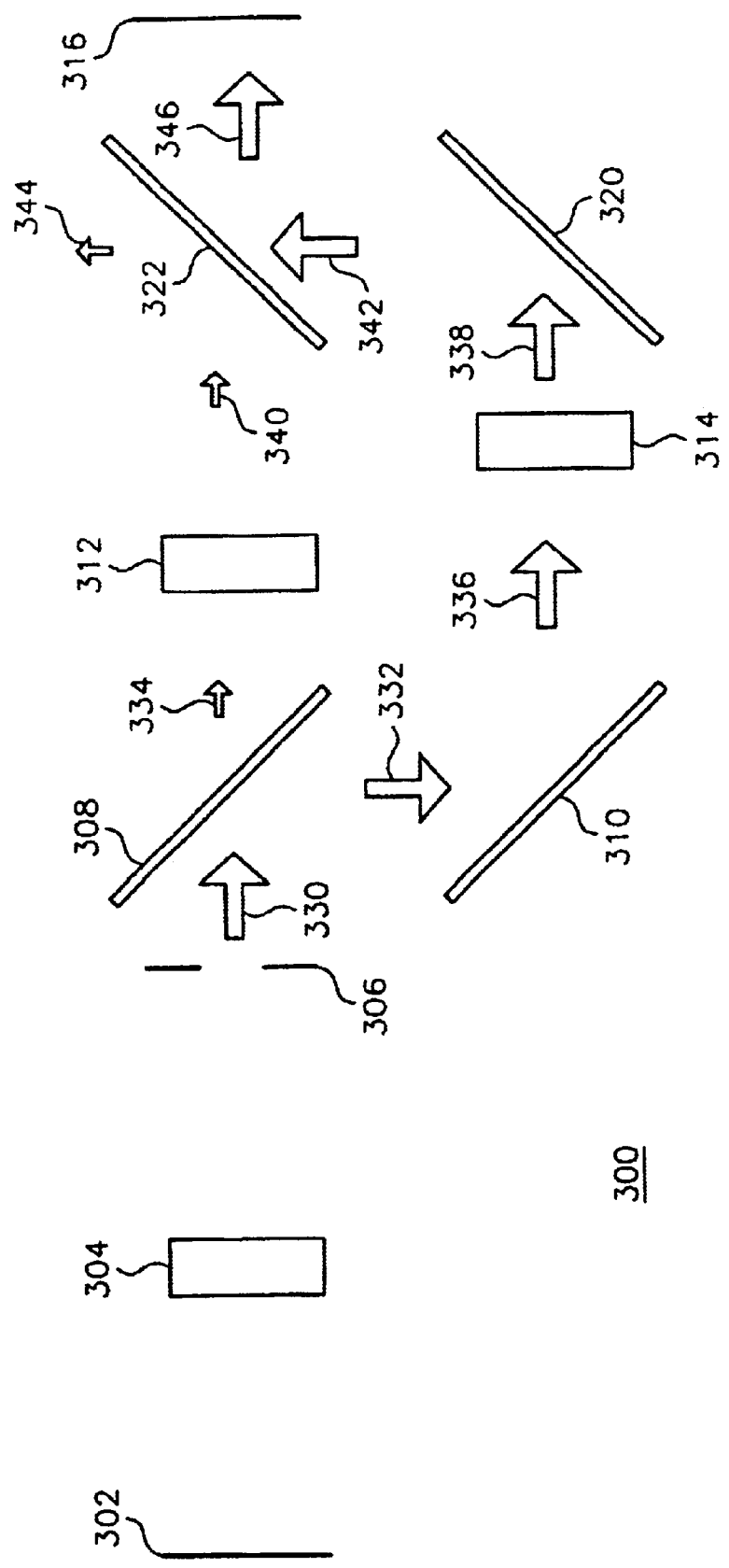

ic chip) to a lead
MULTI-WAVELENGTH APERTURE AND VISION SYSTEM AND METHOD USING SAME This application is a Continuation-in-Part of application Ser. No. 10/336,458 filed on Jan. 3, 2003, now U.S. Pat. No. 6,760,161 which is a Continuation of application Ser. No. 09/961,742 filed on Sep. 24, 2001 and issued as U.S. Pat. No. 6,529,333 on Mar. 3, 2003.

FIELD OF THE INVENTION

This invention relates generally to machine vision systems for semiconductor chip bonding/attaching devices. More specifically, the present invention relates to a multi-wavelength aperture providing different depths of field of an observed object based on a wavelength of light and a system and method using such a multi-wavelength aperture.

BACKGROUND OF THE INVENTION

Semiconductor devices, such as integrated circuit chips, are electrically connected to leads on a lead frame by a process known as wire bonding. The wire bonding operation involves placing and connecting a wire to electrically connect a pad residing on a die (semiconductor chip) to a lead in a lead frame. Once all the pads and leads on the chip and lead frame have been wire bonded, it can be packaged, often in ceramic or plastic, to form an integrated circuit device. In a typical application, a die or chip may have hundreds or thousands of pads and leads that need to be connected.

There are many types of wire bonding equipment. Some use thermal bonding, some use ultra-sonic bonding and some use a combination of both. Prior to bonding, vision systems or image processing systems (systems that capture images, digitize them and use a computer to perform image analysis) are used on wire bonding machines to align devices and guide the machine for correct bonding placement.

Machine vision systems are generally used to inspect the device before, during or after various steps in the fabrication process. During such process steps, it may be necessary to obtain multiple views of the device under different magnification levels to determine whether the device meets predetermined quality standards. One measurement may require a large field of view to include as many fiducials as possible, while a second measurement may require a high resolution to image fine details. Further, these various measurements may need to narrow or expand the depth of field of the observed object in order to view certain details.

In conventional systems, such multiple magnifications are handled by having a separate camera for each desired magnification level. Such a conventional device is shown in FIG. 1. In FIG. 1, imaging device 100 includes objective lens 104, aperture 106, beam splitter 108, mirror 110, relay lenses 112, 114, and cameras 116, 118. In operation an image of device 102 is transmitted through object lens 104 as transmitted image 120 and in turn through aperture 106 as image 122. Image 122 is incident on beam splitter 108, which in turn divides the light from image 122 into first divided light rays 124 and second divided light rays 126. Divided light rays 126 are then redirected by mirror 110 as divided light 128.

Relay lenses 112 and 114 are selected so as to provide the desired magnification of divided light 124 and 128, respectively, resulting in magnified images 130 and 132, which are incident on cameras 116 and 118, respectively. This system has drawbacks, however, in that it requires a separate camera for each level of magnification desired, and also require that multiple apertures be provided to handle different depths of field, thereby resulting in greater complexity and increasing size and cost.

A second conventional system is shown in FIGS. 2A and 2B. In FIGS. 2A and 2B, a shutter 218 is used in combination with a second beam splitter 222 to receive two magnifications of device 202 with a single camera 216. As shown in FIG. 2A, first beamsplitter 208 separates light rays 224 into light rays 226, 228, each being of about equal illumination, that is each of light rays 226, 228 is about half the illumination of light rays 224. When shutter 218 is in a first position, light rays 226 are prevented from reaching relay lens 214. On the other hand, light rays 228 are magnified by relay lens 212 to become magnified light rays 230. In turn, magnified light rays 230 are incident on second beamsplitter 222, a portion (about 50%) of which is transmitted to camera 216 as light rays 236. The remaining portion of magnified light rays 230, however, is deflected by second beamsplitter 222 as lost light rays 234. As a result, only about 25% of the light used to illuminate device 202 is actually received at camera 216. In addition, the inclusion of shutter 218 increases the complexity and cost of this system.

Alternatively, and as shown in FIG. 2B, when shutter is in a second position, light rays 228 are prevented from reaching relay lens 212, while light rays 226 are directed through relay lens 214 by mirrors 210, 220 as magnified light rays 232. Similar to FIG. 2A, a portion 236 of magnified light rays 232 are received by camera 216 while remaining light rays 234 are lost. As is evident, a large portion of the illumination available for imaging is sacrificed due to the losses associated with first beam splitter 208 and second splitter 222. The light from a single channel hits the second splitter and is split into a reflected portion 234 and transmitted portion 236. Only one of these will be directed to camera 216 while the other is lost. This approach can also have reliability issues with respect to the moving shutter mechanism.

SUMMARY OF THE INVENTION

In view of the shortcomings of the prior art, the present invention is directed to an aperture having different effective diameters based on a wavelength of light passing therethrough to provide one of multiple depths of field of the device being viewed.

The present invention is a vision system for use with at least one light source and providing a plurality of images representing plural depths of field of a device. The system comprises a beamsplitter for receiving an image of the device illuminated by the at least one light source, the beamsplitter providing one of the plurality of images of the device based in a wavelength of the light source; an aperture having a plurality of effective diameters based on the wavelength of light from the at least one light source, the aperture determining a depth of field of the image of the device; and an optical element for receiving the image of the device, the optical element magnifying the image by a predetermined magnification factor to produce a magnified image having the determined depth of field.

According to another aspect of the invention, the aperture is a dichroic aperture.

According to a further aspect of the invention, the optical detector is a camera.

According to still another aspect of the invention, the light has a wavelength in the visible spectrum.

According to yet another aspect of the present invention, the beamsplitters are dichroic splitters.

According to a further aspect of the invention, the aperture comprises a first region having a first reactive property to a first wavelength of light from the at least one light source; and a second region adjacent the first region and having a second reactive property to a further wavelength of light from the at least one light source, such that the first reactive property provides a first depth of field of the object and the second reactive property provides a second depth of field of the object.

According to still a further aspect of the invention, the first reactive property results in a first effective diameter of the aperture and the second reactive property results in a second effective diameter of the aperture.

According to yet a further aspect of the invention, the aperture comprises a region having a plurality of reactive properties based on a wavelength of light from the light source; and a further region adjacent the first region and absent a reactive property to any wavelength of light from the light source, such that the plurality of reactive properties provide a respective plurality of a depth of field of the object based on the wavelength of light from the light source.

These and other aspects of the invention are set forth below with reference to the drawings and the description of exemplary embodiments of the invention.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following Figures:

FIGS. 3A and 3B are schematic representations of a vision system according to a first exemplary embodiment of the present invention;

DETAILED DESCRIPTION

Figure 1:
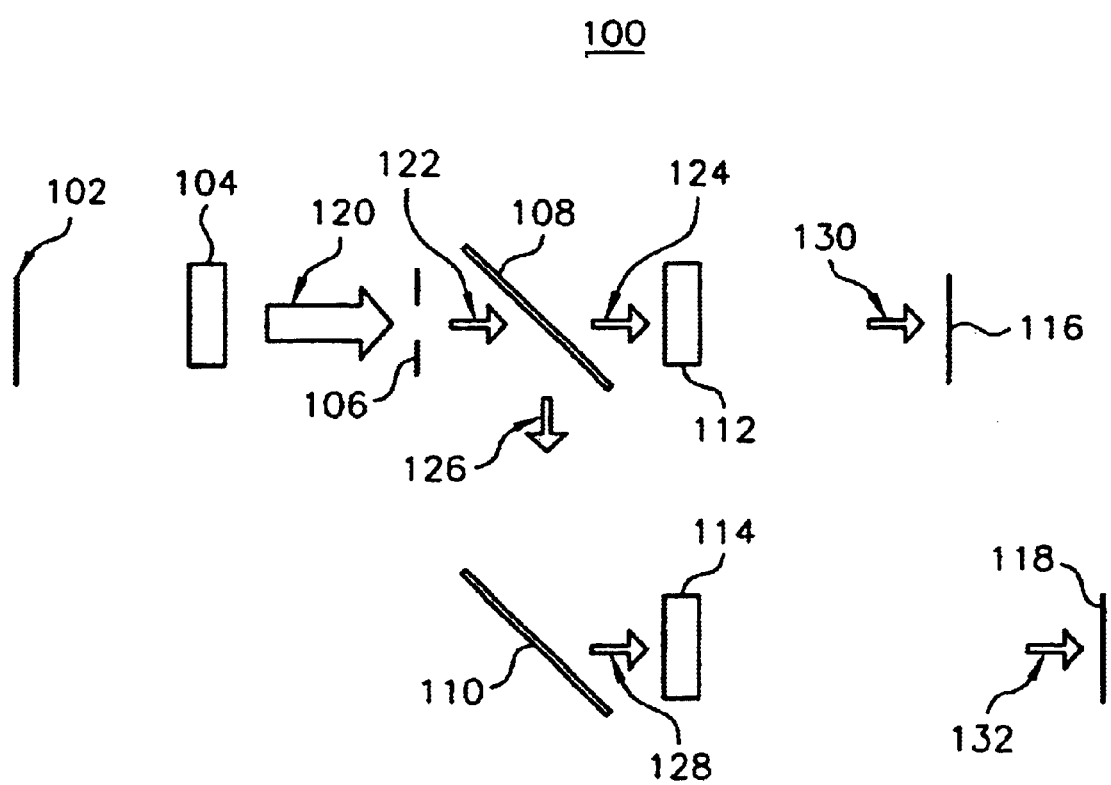
FIG. 1 is schematic representation of a vision system according to the prior art.
Figure 2A:
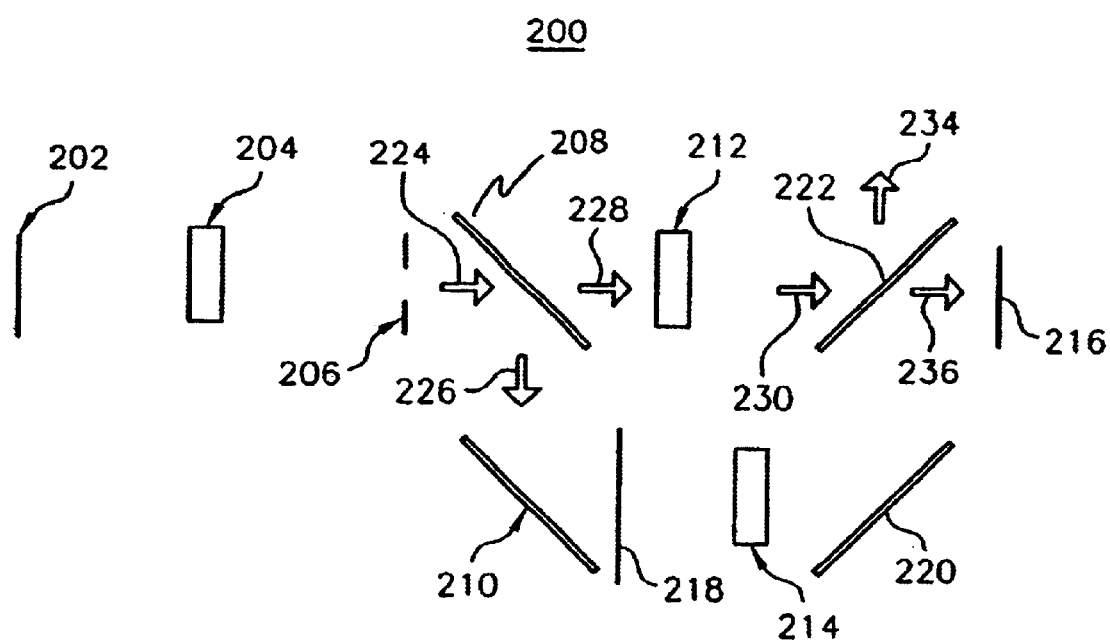
FIGS. 2A and 2B are schematic representations of another vision system according to the prior art.
Figure 2B:
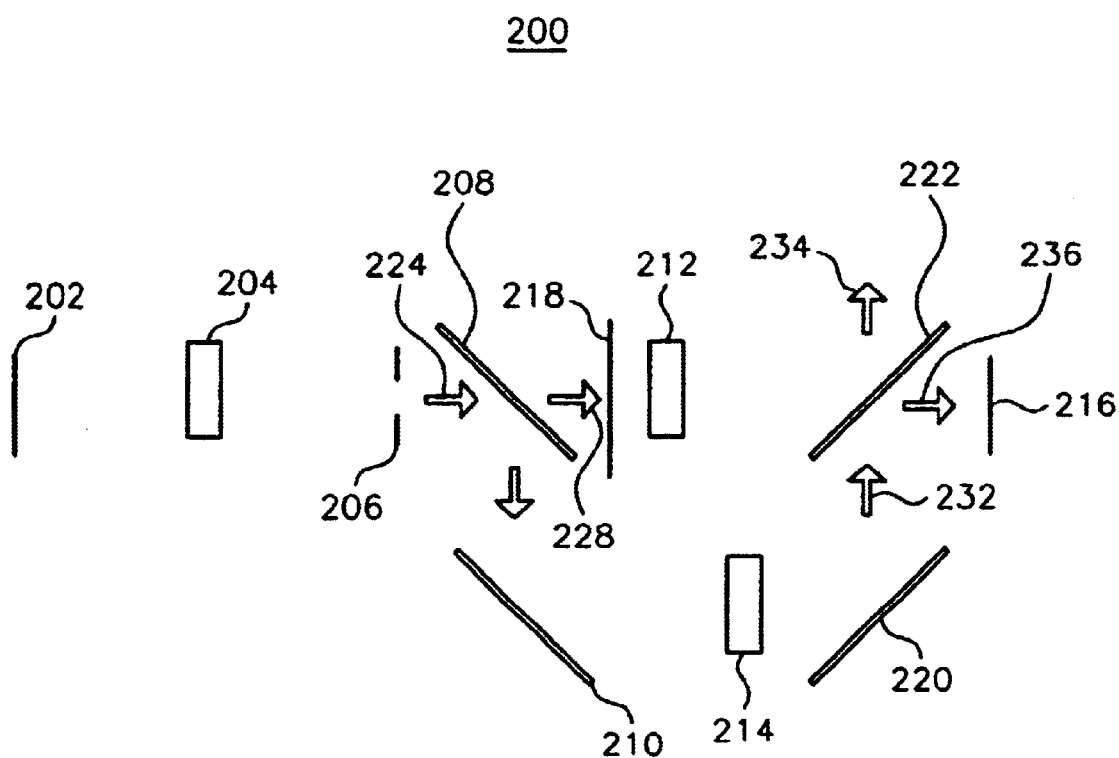
Figure 3B:
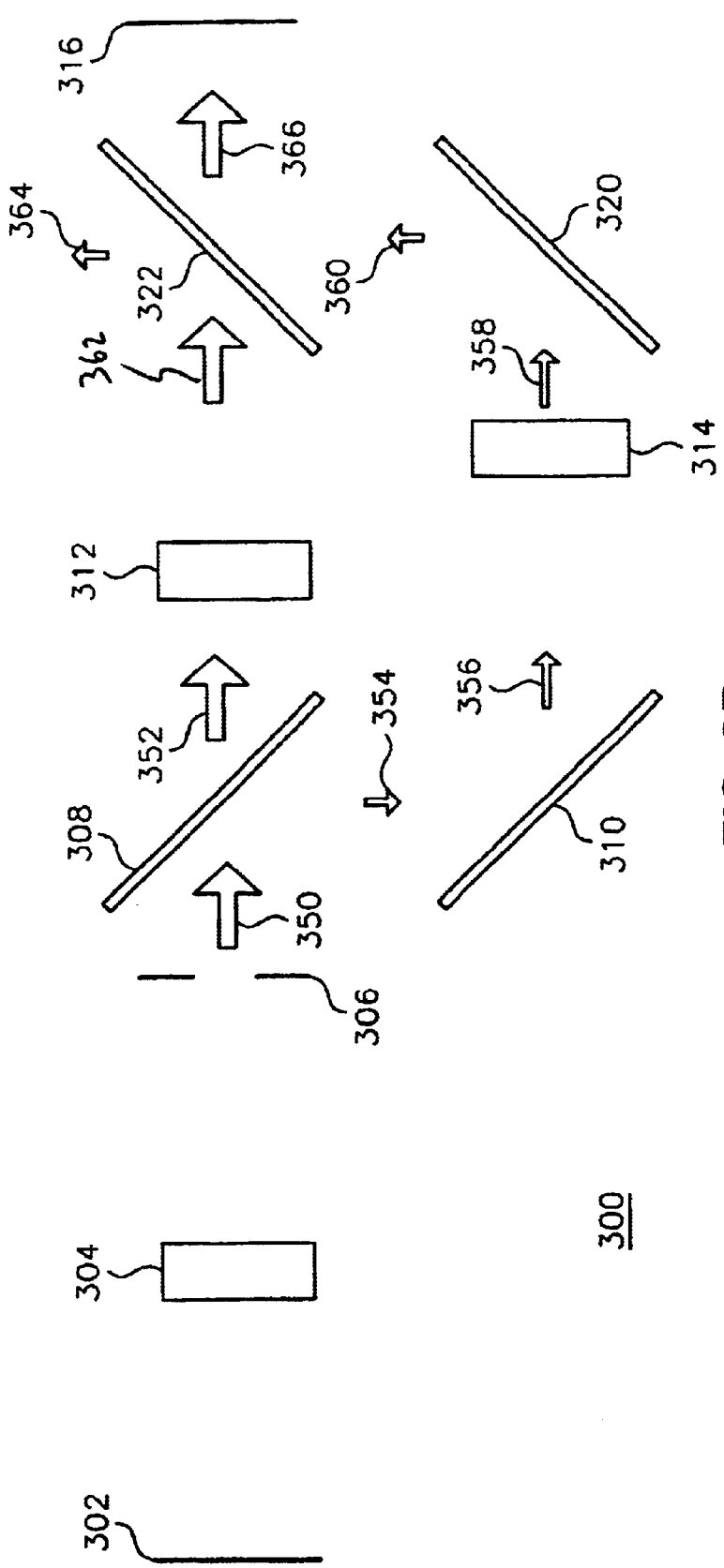

Referring to FIGS. 3A and 3B, an exemplary embodiment of the present invention is shown. In FIG. 3A, device 302 is illuminated by a light source (not shown) having a predetermined wavelength. In a preferred embodiment, this wavelength is within either the visible spectrum of light or ultraviolet spectrum of light. Light rays 330, representing an image of device 302, emerges from lens 304 and aperture 306. Light rays 330 are incident on dichroic splitter 308, which in turn reflects a substantial portion of light rays 330 as reflected light rays 332, based on properties of splitter 308 which are dependent upon the wavelength of light illuminating device 302. As dichroic splitters are not 100% efficient, a small portion of light rays 330 will pass through dichroic splitter 308 as light rays 334. Light rays 332 are then reflected by mirror 310, such as a planar mirror, as light rays 336 so as to allow them to be magnified by optical relay 314. In an exemplary embodiment, optical relay 314 is a doublet type lens assembly having a predetermined magnification factor. Based on this magnification factor, light rays 336 are magnified and emerge from optical relay 314 as magnified light rays 338. As is understood by those of skill in the art, magnified light rays 338 represent an enlarged image of device 302.

Magnified light rays 338 are again redirected by mirror 320 as magnified light rays 342 to be incident on a surface of dichroic splitter 322. In addition, light rays 334, having been magnified by a predetermined magnification factor by optical relay 312, are incident on an opposite surface of dichroic splitter 322 from that of magnified light rays 342. In an exemplary embodiment, the magnification factors of optical relays 312 and 314 are different from one another. Dichroic splitter 322 has properties, based on the wavelength of light illuminating device 302, such that the undesired image rays 340 do not pass through splitter 322, but rather are reflected away as discarded light 344. In this way multiple images are not provided to optical detector 316. On the other hand, dichroic splitter 322 has properties, based on the wavelength of light illuminating device 302, allowing magnified light rays 342 to be directed toward optical detector 316 as image rays 346. As a result, optical detector 316 "sees" only a single magnified image of device 302. In a preferred embodiment of the present invention optical detector 316 may be a camera, such as a CCD or CMOS camera, or a position sensitive detector (PSD).

Referring now to FIG. 3B, device 302 is illuminated by a light source (not shown) having a predetermined wavelength different from the wavelength of light that illuminated device 302 as described above with respect to FIG. 3A. In a preferred embodiment, this wavelength is within the visible spectrum of light. In FIG. 3B, light rays 350, representing another image of device 302, emerges from lens 304 and aperture 306. Light rays 350 are incident on dichroic splitter 308, which in turn passes a substantial portion of light rays 350 as light rays 352, based on properties of splitter 308 which depend upon the wavelength of light illuminating device 302. Once again, as dichroic splitters as not 100% efficient, a small portion of light rays 350 will be reflected by dichroic splitter 308 as reflected light rays 354. These light rays will in turn be redirected by mirror 310 as light rays 356, which will in turn be magnified by optical relay 314 as magnified light rays 358, which are then redirected toward dichroic splitter 322 by mirror 320 as reflected light 360.

Light rays 352 that emerge from dichroic splitter 308, pass through and are magnified by optical relay 312 to become magnified light rays 362. As a result, magnified light rays 362 are incident on dichroic splitter 322. As discussed above with respect to FIG. 3A, dichroic splitter 322 has properties, based on the wavelength of light illuminating device 302, such that undesired light rays 360 pass through splitter 322, and thus are directed away from optical detector 316 as discarded light 364. On the other hand, dichroic splitter 322 has properties, based on the wavelength of light illuminating device 302, allowing magnified light rays 362 to pass through splitter 322 as image rays 366. It is image rays 366 which are now "seen" by optical detector 316. In this way multiple images are not provided to optical detector 316 and different magnifications of device 302 may be provided merely by changing the wavelength of light that illuminates device 302.

Figure 4:
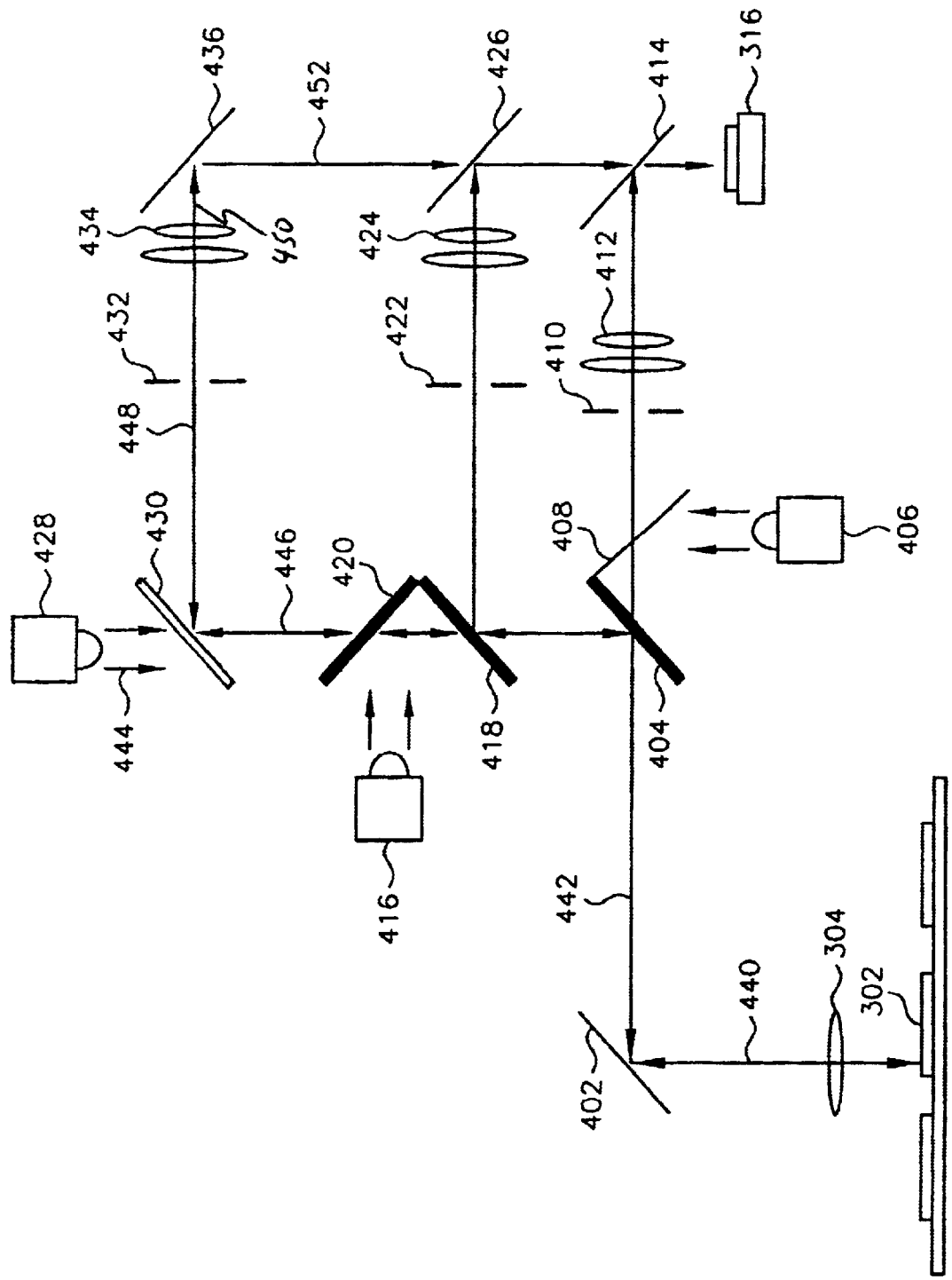
FIG. 4 is a schematic representation of a vision system according to a second exemplary embodiment of the present invention.

FIG. 4 illustrates a second exemplary embodiment of the present invention in which more that two light sources are used to illuminate device 302 and provide more than two different magnifications of device 302. In FIG. 4, device 302 is illuminated by one of light sources 406, 416, 428, each having a different wavelength. In a preferred embodiment, these wavelengths are within either the visible spectrum of light or ultraviolet spectrum of light. Illumination emitted by each of light sources is directed toward device 302 though a series of dichroic splitters 404, 418, 420, and 430. In the exemplary embodiment, only one light source is used to illuminate device 302 depending on the magnification desired. In the example illustrated in FIG. 4, light source 406 is used to provide magnification of device 302 through lens 412, light source 416 is used to provide magnification of device 302 through lens 424, and light source 428 is used to provide magnification of device 302 through lens 434. The magnification factor of each of lenses 412, 424, 434 is selected as desired. In a preferred embodiment of the present invention the magnification factor of lenses 412, 424, 434 is 2×, 6×, and 8×, respectively.

To illustrate how the second exemplary embodiment functions, a specific example is now discussed. If for example, it is desired to magnify an image of device 302 by a specific magnification factor achieved through lens 434, light source 428 is activated and the remaining light sources 406, 416 are deactivated. Light rays 444 pass through dichroic splitters 430, 420 and 418 and are reflected by dichroic splitter 404 based on the wavelength of the light rays. These light rays are then re-directed by mirror 402 to illuminate device 302. In turn, light rays 440, representing an image of device 302, emerges from lens 304, are reflected by mirror 402 as reflected light rays 442 and directed toward dichroic splitter 404. As mentioned above, the wavelength of the light rays 446 are such that they are reflected by splitter 404 and pass through splitters 418, 420. The bottom surface of splitter 430 has different properties than that of the top surface of splitter 430. As a result, light ray 446 are reflected by splitter 430 rather than passing through it. These reflected rays 448 pass through aperture 432 and are in turn magnified by lens 434. Light rays 450, representing the magnified image of a portion of device 302 are next redirected by mirror 436 as reflected light rays 452, which in turn, based on the wavelength of the light rays, pass through dichroic splitters 426 and 414, and are received by detector 316, such as a CCD or CMOS camera, or a position sensitive detector (PSD). As such, detector 316 received a magnified image of device 302 based on the wavelength of the light used to illuminate the device. Similarly, the path of light used to illuminate device 302 and its reflected image is based on the wavelength of light sources 406 and 416.

Figure 5A:
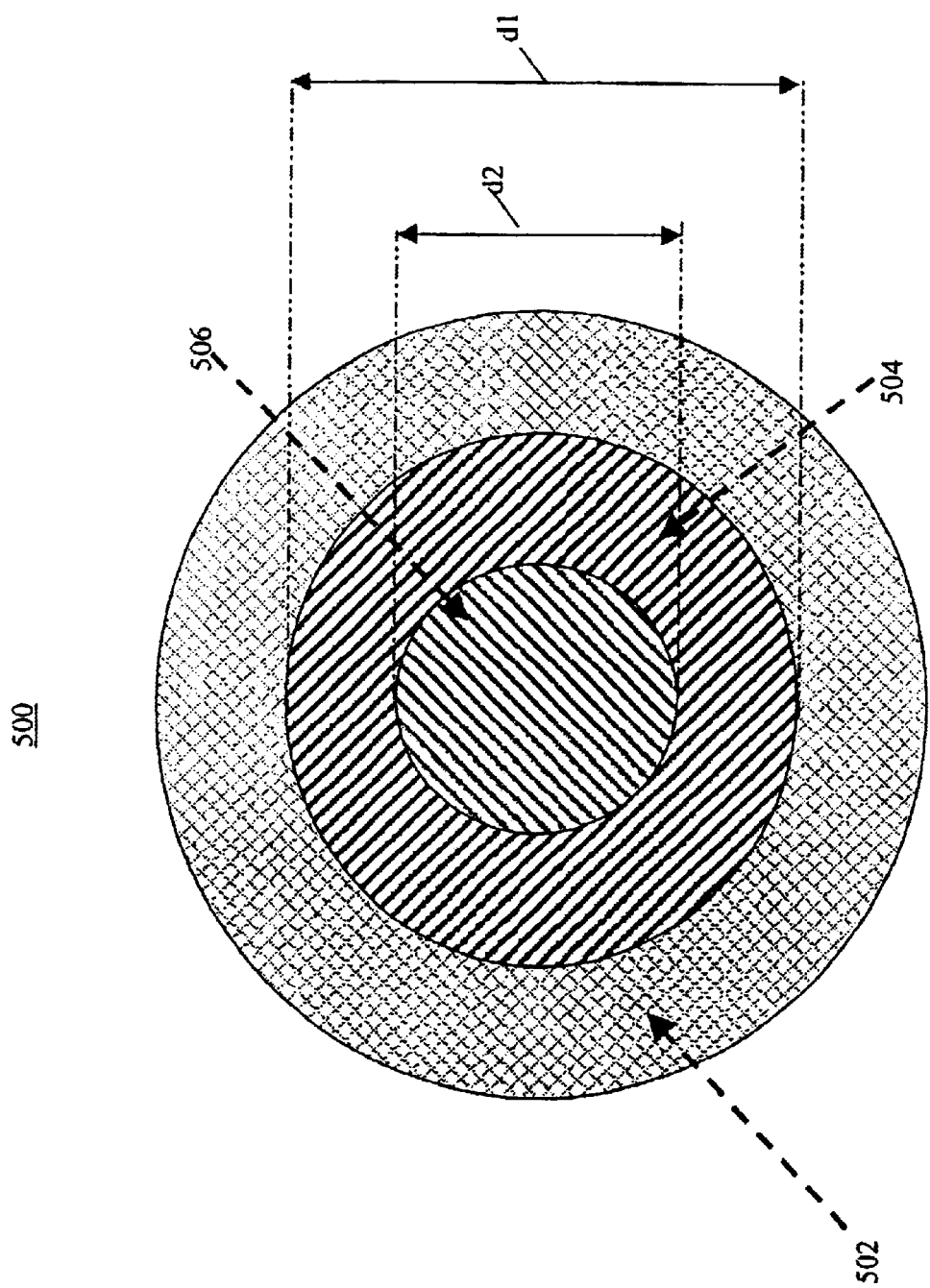
FIGS. 5A–5C are views of a dichroic aperture according to an exemplary embodiment of the present invention.
Figure 5C:
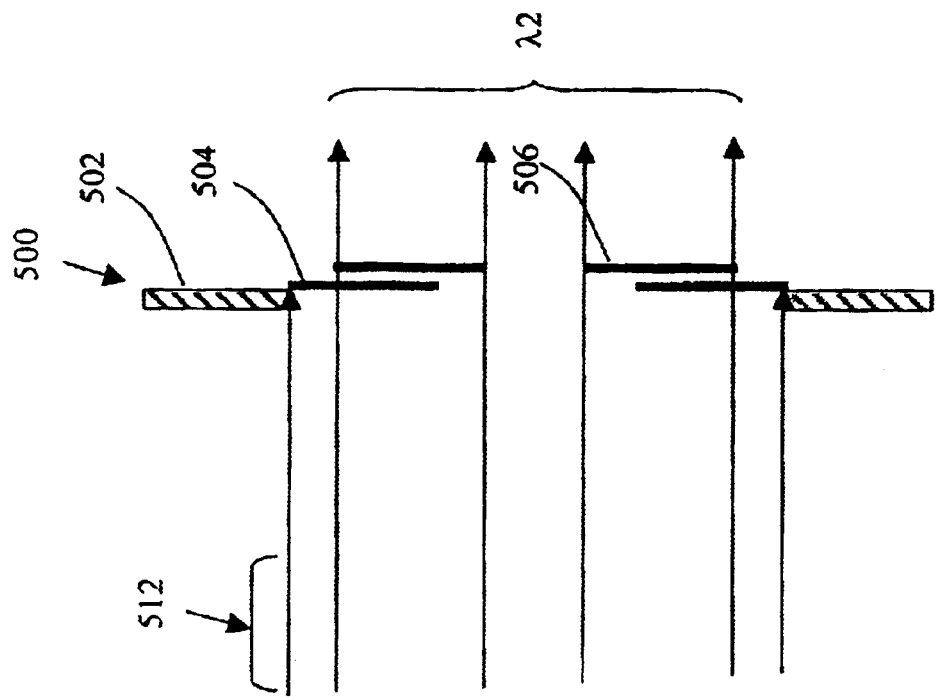
Figure 5B:
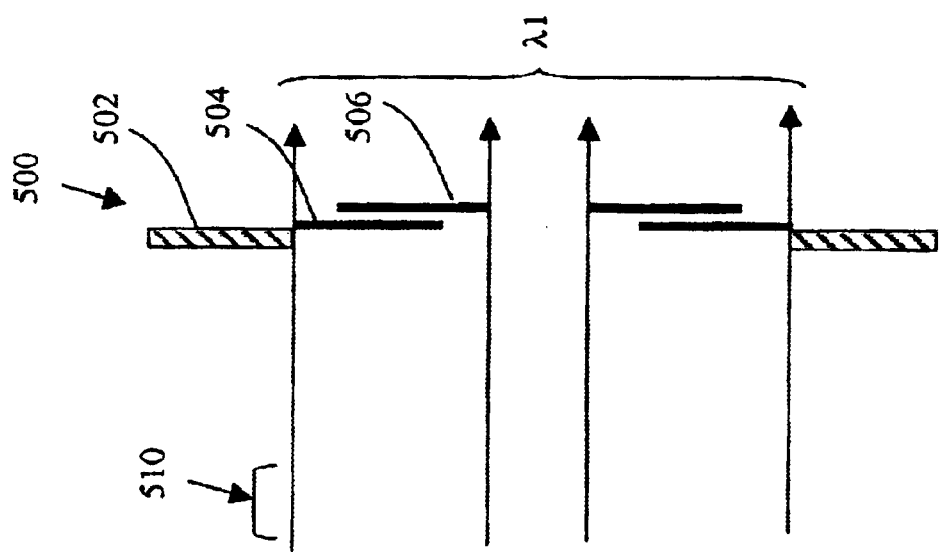

Referring now to FIGS. 5A–5C, an exemplary dichroic aperture 500 has various regions 502, 504 and 506. As shown in FIG. 5A, in aperture 500, region 502 represents a portion of the aperture where no light can penetrate, region 504 has a diameter d1 and represents a portion where light having a first wavelength λ1 can penetrate, and region 506 has a diameter d2 smaller than d1 and represents a portion where light having a second wavelength λ2 can penetrate. With respect to region 506, light having the first wavelength will also pass through this region. As is known to those skilled in the optical arts, the diameter of an optical aperture affects the depth of field (DOF) and Modulation Transfer Function (MTF) (or optical resolution) of the object being observed. Therefore, as a result of illuminating the object to be observed by light having different wavelengths (in this example λ1 or λ2), the DOF and MTF may be controlled. For example, and as shown in FIGS. 5B and 5C, if light having wavelength λ1 is used, aperture 500 has diameter d1 resulting in a short DOF 510 and a greater MTF. On the other hand, if light having a wavelength λ2 is used, aperture 500 has a diameter d2 resulting in a greater DOF 512 and lower MTF. Although not shown in FIG. 5C, the portion of light having wavelength λ2 that does not pass through aperture 500 is reflected.

Figure 5D:
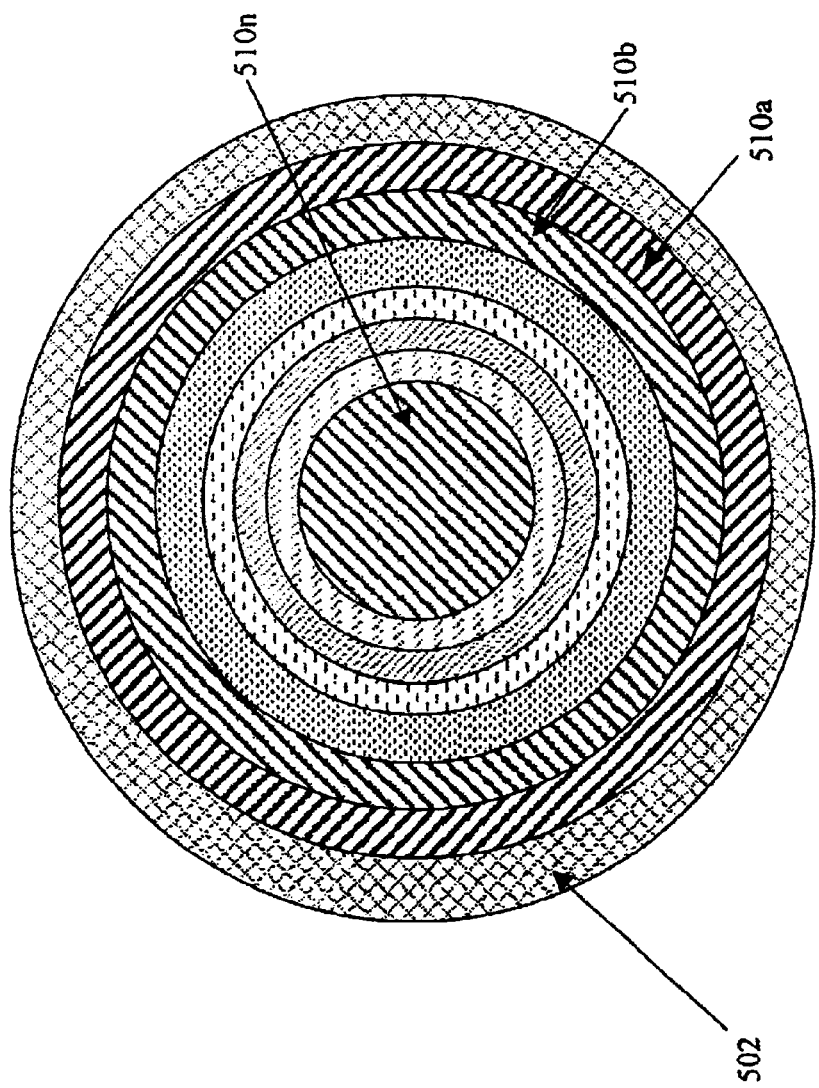
FIG. 5D is a plan view of a dichroic aperture according to another exemplary embodiment of the present invention.

Dichroic aperture 500 may be formed using well-known thin film coating and masking techniques, for example. Although the exemplary dichroic aperture 500 is illustrated with two regions (504, 506), the invention is not so limited. As shown in FIG. 5D, for example, it is contemplated that any number of regions may 510a, 510b, . . . 510n be provided, each tuned to a different wavelength of light, to provide a variety of Depths of Field, as desired.

Figure 6:
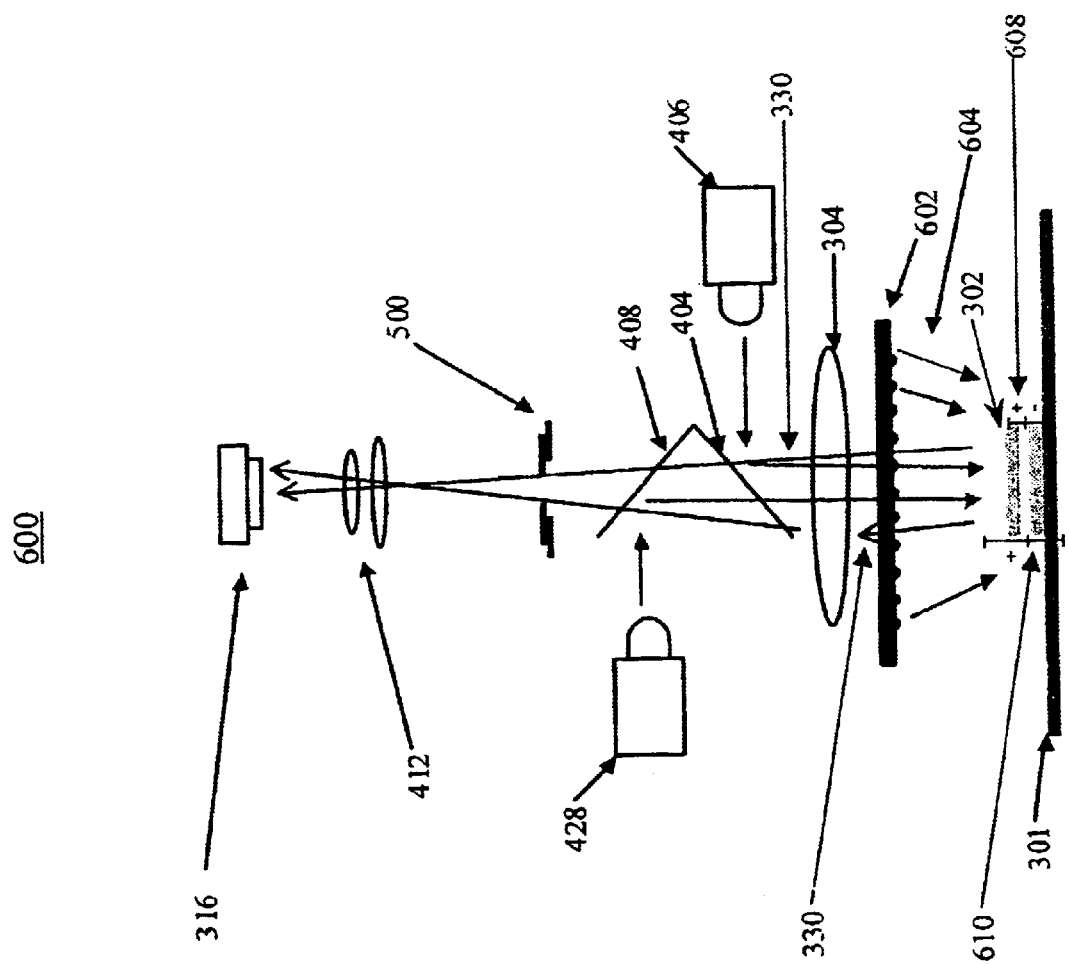
FIG. 6 is a schematic representation of a vision system according to an exemplary embodiment of the present invention utilizing an exemplary dichroic aperture.

Referring now to FIG. 6, an exemplary embodiment of a vision system 600 using dichroic aperture 500 is illustrated. In FIG. 6, device 302 is illuminated by light source 602 having light rays 604 of a predetermined wavelength and/or light sources 406 or 428 also having a wavelength equal to that of light source 602. Light source 602 may be capable of providing illumination in one or more discrete wavelengths as desired. Further light source 602 may be combined with either light source 406 or 428 to provide both oblique and perpendicular illumination to device 302. Those of skill in the art understand that, although it is desirable for the wavelength of light source 406 or 428 to be equal to that of light source 602, due to manufacturing tolerances the wavelengths may vary slightly. Similar to the embodiment described above, illumination for light sources 406, 428 are incident on device 302 via dichroic splitters 404, 408.

Light rays 330, representing an image of device 302, emerge from lens 304, such as an achromatic or chromatic lens as desired. Light rays 330 are incident on dichroic splitters 404, 408, which in turn reflect a portion of light rays 330 as reflected light rays (not shown), based on properties of splitter 308 which are dependant upon the wavelength of light source 602. The remaining light is incident on dichroic aperture 500. Based on the wavelength of the light, dichroic aperture 500 adjusts its effective diameter as discussed above and passes the light onto relay lens 412, such as an achromatic lens having a predetermined magnification factor, either positive or negative. This resultant image is incident on optical detector 316. Because of the reaction of dichroic aperture to the wavelength of light from light sources 602, 406, 428 on device 302, the depth of field may be either narrow 608 or deep 610.

In another exemplary embodiment, light source 602 may have a variable wavelength to adjust the DOF of the object being observed, as desired.

Although the exemplary embodiment illustrates three light sources 602, 406, 428, the invention is not so limited. It is also possible to add additional light sources similar to those of 406, 428 with appropriate dichroic splitters as desired. Of course, as the number of available wavelengths increase, the number of active areas in dichroic aperture 500 should also increase by a like number.

Figure 7A:
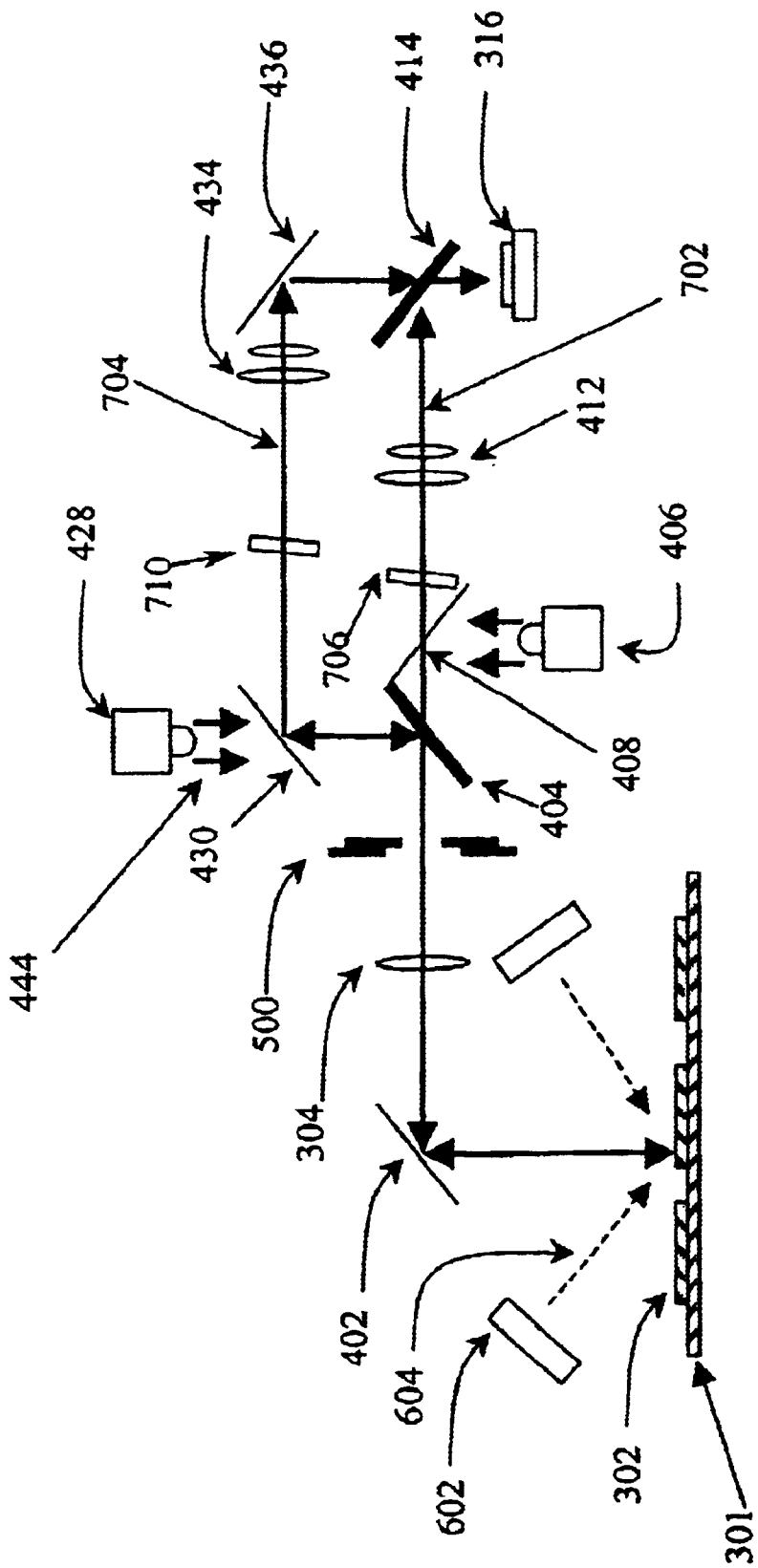
FIGS. 7A–7B are a schematic representations of vision systems according to another exemplary embodiment of the present invention utilizing an exemplary dichroic aperture.
Figure 7B:
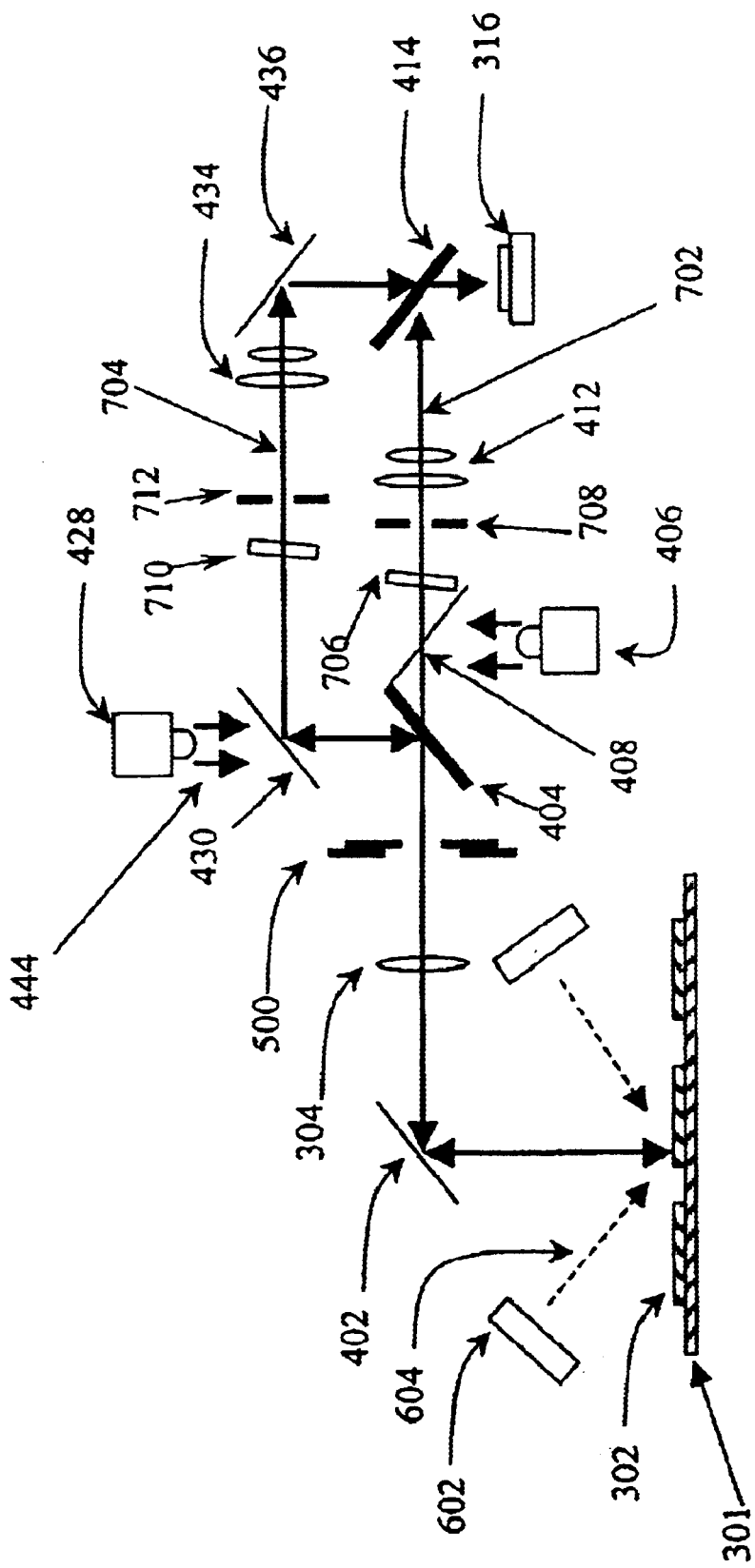

FIGS. 7A–7B illustrate other exemplary embodiments of the present invention in which dichroic aperture 500 is incorporated into the embodiment described above with respect to FIG. 4. In an effort to provide a more concise representation, however, this exemplary embodiment addresses only two magnification paths, rather that the three magnification paths of FIG. 4. The invention is not so limited and it is contemplated that the invention may be used with any number of light sources (including variable wavelength light sources) and magnification paths, as desired.

As shown in FIG. 7A, device 302, disposed on substrate 301 for example, is illuminated by one of light sources 406, 428, each having a different wavelength. In a preferred embodiment, these wavelengths are within either the visible spectrum of light or ultraviolet spectrum of light. Illumination emitted by each of light sources is directed toward device 302 though a series of dichroic splitters 404, 408, and 430 and dichroic aperture 500. Light for the one active light source 406, 428 changes the effective diameter of dichroic aperture 500, thereby adjusting the DOF of observed device 302.

In the exemplary embodiment of FIG. 7, only one light source at a time is used to illuminate device 302 depending on the desired magnification and DOF. For example, light source 406 is used to provide magnification of device 302 through lens 412 at a first DOF, and light source 428 is used to provide magnification of device 302 through lens 434 at a second DOF. The magnification factor of each of lenses 412, 434 is selected as desired, as is the DOF. In a non-limiting exemplary embodiment of the present invention, the magnification factor of lenses 412, 434 is 2×, and 8×, respectively. Furthermore, filters 706, 710 may be added to respective magnification paths as desired to eliminate cross coupling between the wavelengths of light by removing any remaining undesired wavelengths of light that may have passed through dichroic splitters 404, 406, and 430. Additionally, and as shown in FIG. 7B, achromatic apertures 708, 712 may also be added to eliminate stray light that may be present in light rays 702, 704 respectively.

As can be appreciated by one of skill in the art, this approach may be modified and expanded to use more than two light sources and magnification paths as desired.

Although the invention has been described with reference to exemplary embodiments, it is not limited thereto. Rather, the appended claims should be construed to include other variants and embodiments of the invention which may be made by those skilled in the art without departing from the true spirit and scope of the present invention.

What is claimed:

1. A vision system for use with at least one light source and providing a plurality of images representing plural depths of field of a device, the system comprising:
    a beamsplitter for receiving an image of the device illuminated by the at least one light source, the beamsplitter providing one of the plurality of images of the device based in a wavelength of the light source;
    an aperture having a plurality of effective diameters based on the wavelength of light from the at least one light source, the aperture determining a depth of field of the image of the device; and
    an optical element for receiving the image of the device, the optical element magnifying the image by a predetermined magnification factor to produce a magnified image having the determined depth of field.

2. The vision system according to claim 1, wherein the aperture is a dichroic aperture.

3. The vision system according to claim 1, further comprising an optical detector to receive the magnified image.

4. The vision system according to claim 3, wherein the optical detector is a camera.

5. The vision system according to claim 3, wherein the optical detector is a position sensitive detector.

6. The vision system according to claim 1, wherein the light has a wavelength in one of i) a visible spectrum and ii) an ultraviolet spectrum.

7. The vision system according to claim 1, wherein the beamsplitter is a dichroic splitter.

8. The vision system according to claim 1, wherein the plurality of optical elements is at least one lens.

9. The vision system according to claim 8, wherein the at least one lens has a predetermined magnification factor.

10. The vision system according to claim 1, wherein the at least one light source is a monochromatic light source.

11. The vision system according to claim 1, wherein the at least one light source is a plurality of monochromatic light sources, each of the plurality of light sources having a respective wavelength.

12. The vision system according to claim 1, wherein the at least one light source is i) a first light source comprising a plurality of monochromatic light sources and ii) at least one further light monochromatic source.

13. The vision system according to claim 1, wherein the at least one light source is i) a first light source comprising a plurality of monochromatic light sources and ii) a respective plurality of further light monochromatic sources, each of the plurality of further light monochromatic sources having a wavelength equal to a wavelength of a respective one of the plurality of monochromatic light sources.

14. A vision system for use with at least one light source and providing a plurality of images representing plural depths of field of a device, the system comprising:
    a first beamsplitter for receiving an image of the device illuminated by the at least one light source, the beamsplitter providing a plurality of images of the device;
    an aperture having a plurality of effective diameters based on a wavelength of light from the at least one light source, the aperture determining a depth of field of the plurality of images of the device;
    a plurality of optical elements for receiving respective ones of the plural images of the device, each of the plurality of optical elements magnifying the image by a predetermined magnification factor to produce a plurality of magnified images; and
    a second beamsplitter for receiving the plurality of magnified images and filtering the magnified images based on a wavelength of the light source.

15. A method for providing a plurality of images representing plural depths of field of a device, the method comprising the steps of:
    illuminating the device with light having a first wavelength;
    receiving an image of the device illuminated by the light;
    adjusting a depth of field of the image based on the first wavelength of the light; and
    providing the image to an optical detector.

16. A method for providing a plurality of magnified images of a device, the method comprising the steps of:
    illuminating the device with a light;
    receiving an image of the device illuminated by the light;
    adjusting a depth of field of the image of the device based on the a wavelength of the light;
    providing a plurality of images of the device based on the wavelength of the light;
    receiving respective ones of the plural images of the device;

magnifying each of the respective ones of the plural images of the device by a predetermined magnification factor to produce a plurality of magnified images;

receiving the plurality of magnified images; and detecting one of the plurality of magnified images based on the wavelength of the light.

17. A vision system for use with a light source having a plurality of wavelengths of light and providing a plurality of images of a device, the system comprising:

a first beamsplitter for receiving an image of the device illuminated by a first wavelength of light of the light source, the beamsplitter providing a first image of the device;

a second beamsplitter for receiving an image of the device illuminated by a second wavelength of light of the light source, the beamsplitter providing a second image of the device;

an aperture having a plurality of effective diameters based on a wavelength of the light source, the aperture determining a depth of field of the image of the device;

a plurality of optical elements for receiving a respective one of the first and second images of the device, each of the plurality of optical elements magnifying the image by a predetermined magnification factor to produce a respective magnified image; and a detector for receiving one of the magnified images based on the wavelength of light from the light source illuminating the device.

18. The vision system according to claim 17, wherein the light source has a variable light wavelength.

19. The vision system according to claim 17, wherein the light source has a plurality of discrete light wavelengths.

20. The vision system according to claim 17, wherein the light source is at least two light sources.

21. A vision system for use with a plurality of light wavelengths and providing a respective plurality of images of a device, the system comprising:

a first beamsplitter for receiving an image of the device illuminated by a first one of the plurality of light wavelengths, the beamsplitter providing a first image of the device;

a second beamsplitter for receiving an image of the device illuminated by a second one of the plurality of light wavelengths, the beamsplitter providing a second image of the device;

a third beamsplitter for receiving an image of the device illuminated by a third one of the plurality of light wavelengths, the beamsplitter providing a third image of the device;

an aperture having a plurality of effective diameters based on respective wavelengths of the plurality of light wavelengths, the aperture determining a depth of field of the image of the device;

a plurality of optical elements for receiving a respective one of the first, second and third images of the device, each of the plurality of optical elements magnifying the image by a predetermined magnification factor to produce a respective magnified image; and a detector for receiving one of the magnified images based on which of the plurality of light wavelengths illuminates the device.

22. The vision system according to claim 21, wherein each of the plurality of light wavelengths is different from that of the remaining plurality of light wavelengths.

23. The vision system according to claim 21, wherein the plurality of light wavelengths is at least three light wavelengths.

* * * * *